United States Patent [19]

Murakami et al.

[11] Patent Number: 5,190,906
[45] Date of Patent: Mar. 2, 1993

[54] ALKYL AROMATIC HYDROCARBON DEHYDROGENATION CATALYST AND METHOD FOR PRODUCING THE CATALYST

[75] Inventors: Akira Murakami, Toyama; Hidemi Unei, Tokyo; Masayuki Teranishi, Saitama; Masaki Ohta, Toyama, all of Japan

[73] Assignee: Nissan Girdler Catalyst Co., Ltd., Tokyo, Japan

[21] Appl. No.: 843,919

[22] Filed: Feb. 27, 1992

[30] Foreign Application Priority Data

Mar. 5, 1991 [JP] Japan .................................. 3-123185

[51] Int. Cl.$^5$ ........................ B01J 21/06; B01J 23/10; B01J 23/78; B01J 23/86; B01J 23/88
[52] U.S. Cl. .................................. 502/304; 502/309; 502/330; 585/444
[58] Field of Search ........................ 502/304, 309, 330; 585/444

[56] References Cited

U.S. PATENT DOCUMENTS

| | | | |
|---|---|---|---|
| 2,932,673 | 4/1960 | Melik et al. | 585/444 X |
| 3,084,125 | 4/1963 | Soderquist et al. | 252/430 |
| 3,291,756 | 12/1966 | Bowman | 252/474 |
| 3,361,633 | 1/1968 | Gutmann | 252/470 |
| 3,387,053 | 6/1968 | Lee | 260/669 |
| 3,542,897 | 11/1970 | Wattimena et al. | 260/683.3 |
| 3,904,552 | 9/1975 | O'Hara | 252/458 |
| 4,134,858 | 1/1979 | Courty | 252/455 R |
| 4,504,594 | 3/1985 | Chu | 502/330 X |
| 4,749,674 | 1/1988 | Dejaifve et al. | 502/304 |
| 5,023,225 | 6/1991 | Williams et al. | 502/304 |

FOREIGN PATENT DOCUMENTS

| | | |
|---|---|---|
| 63-316746 | 12/1988 | Japan . |
| 680509 | 10/1952 | United Kingdom . |

*Primary Examiner*—W. J. Shine
*Attorney, Agent, or Firm*—Whitham & Marhoefer

[57] ABSTRACT

In order to increase performances of an iron oxide-potassium oxide system catalyst to be used for an alkyl aromatic hydrocarbon dehydrogenation reaction in the presence of steam, there is provided an alkyl aromatic hydrocarbon dehydrogenation catalyst wherein a little amount of titanium oxide is added by the mixing and kneading method or by the preceding addition to iron oxide in the production of the iron oxide-potassium oxide system catalyst to be used for the alkyl aromatic hydrocarbon dehydrogenation reaction in the presence of steam. The iron oxide-potassium oxide system catalyst is allowed to contain a little amount of titanium oxide, whereby an activity can be remarkably increased, as well as a selectivity in the same conversion ratio can also be improved in the alkyl aromatic hydrocarbon dehydrogenation reaction, and further the obtained catalyst exhibits stable performances with time on stream.

7 Claims, No Drawings

ALKYL AROMATIC HYDROCARBON DEHYDROGENATION CATALYST AND METHOD FOR PRODUCING THE CATALYST

FIELD OF THE INVENTION

The present invention relates to a catalyst for producing alkenyl aromatic hydrocarbons such as styrene and the like by means of dehydrogenation of alkyl aromatic hydrocarbons such as ethylbenzene and the like in the presence of steam.

BACKGROUND OF THE INVENTION

Styrene is usually produced by dehydrogenation of ethylbenzene, which is used as a raw material monomer for synthetic rubber, ABS resin, polystyrene and the like, so that its production amount is increasing year by year.

The ethylbenzene dehydrogenation reaction is an endothermic reaction accompanied by expansion of volume as shown by the following reaction formula:

$$C_6H_5 \cdot C_2H_5 \rightarrow C_6H_5 \cdot C_2H_3 + H_2 - 113 \text{ kilojoules/mol}$$

This reaction was actively studied in 1940th in the United States in order to meet the social requirement for the production of synthetic rubber, during which there has been technically established a system in which ethylbenzene is catalytically dehydrogenated under steam dilution as industrially carried out at present, resulting in occupying a position as a representative production method of styrene.

The volume is expanded in this reaction, so that it is advantageous from a viewpoint of chemical equilibrium to dilute the reactants with steam, and the steam dilution has the following advantages other than the above.

(a) The reaction is performed at a high temperature of 550° C. to 650° C., so that steam can be utilized as a heat source for heating ethylbenzene.

(b) Although carbonaceous substances deposit on the catalyst due to side reactions, a water gas reaction with steam can be utilized for removing them, whereby continuous use can be conducted without regeneration of the catalyst.

(c) The steam as the diluent can be easily separated from the product only by liquefying the product.

As described above, the dehydrogenation reaction system in the presence of steam is an industrially excellent production method in which styrene can be continuously produced under an advantageous condition from a viewpoint of chemical equilibrium, and the foregoing operation method has become technically available owing to the fact that it has been revealed that the iron oxide-potassium oxide system catalyst stably maintains its high performance without poisoning by steam, however, before the catalyst became industrially available, many further improvements in performance had been contemplated, during which addition of various promoter components had been investigated.

The role of each catalyst component has been scholarly elucidated under a situation of reaction, wherein the component which has an activity on the dehydrogenation reaction itself is partially reduced iron oxide, and potassium oxide acts as the promoter to enhance the activity of iron oxide and promotes the water gas reaction of steam with the carbonaceous substances deposited on the surface of the catalyst so as to prevent time-dependent deterioration of the activity, and other promoter components are added in order that the activity and selectivity are increased or the thermal stability, mechanical strength stability and the like of the catalyst are increased.

The catalyst is usually produced such that iron oxide or an iron compound as its precursor, a potassium compound and other promoter component oxides or precursor compounds thereof are mixed and kneaded in the co-presence of moisture, and then extrusion molding, drying and calcination are performed.

Those used as raw iron materials are red iron oxide (hematite) or yellow oxy-iron hydroxide (goethite) as its precursor compound and the like, and the raw potassium materials are those which can be decomposed into potassium oxide by calcination, for which any compound can be used provided that no component which gives a poisoning action is allowed to remain in the catalyst, however, potassium hydroxide, potassium carbonate or the like is usually used.

Iron oxide and potassium oxide are essential components provided that the ethylbenzene dehydrogenation reaction is performed in the presence of dilution steam, and the combination of the both components greatly enhances the activity of iron oxide as compared with the case in which it is used alone, however, only the both components were insufficient to use as an industrial catalyst, and in order to improve the activity as well as the selectivity, stability of catalyst structure, mechanical strength and the like, various promoter components to meet with the object have been added and supplied as commercial catalysts.

As the promoter components to be added, for example, are known Ce, Cr and the like as a component for increasing the activity, Ca, V, Mo, W and the like as a component for increasing the selectivity, and as the prior art in which these elements are used are proposed addition of Ce, Mo, Ca, Mg or Cr in U.S. Pat. No. 5,023,225, addition of Cr, Mo, W, V and Al in German Patent DE4025931, and addition of Ca, Ce, Ge, Sn, Pb and the like in Japanese Patent Laid-open No. 64-27646 respectively, while as components for contributing to the structural stability of the catalyst are known Cr, Mg and the like which are disclosed in U.S. Pat. No. 5,023,225 or DE4025931 together with the components for increasing the performance, however, as a component for stabilizing the catalyst structure being different from these elements, addition of Ti is disclosed in Czechoslovakia Patent CS168220 and 174488 respectively.

The addition of these promoter components greatly increases the catalyst performance and improves the stability of catalyst structure or mechanical strength, however, the dehydrogenation catalyst has a high alkali metal content and is used at a high reaction temperature in spite of the high alkali content, so that problems such as migration of the alkali metal in the catalyst, scattering toward the downstream side of the catalyst layer and the like are apt to take place in the practical operation, which result in the decrease in catalyst performance or the increase in pressure drop due to blockade of the catalyst layer, and hence a danger of giving a trouble for the operation of equipment is included, while its activity is fairly low as compared with the equilibrium conversion ratio of ethylbenzene at a practical industrial reaction temperature, remaining a room to be improved from a viewpoint of performance.

Here, when the ethylbenzene dehydrogenation reaction is considered from an industrial viewpoint, if the activity can be increased without deteriorating the selectivity of the catalyst, then not only the yield of styrene can be increased, but also an operation under a more moderate condition is made possible, so that it becomes possible to provide countermeasures for reducing various operational problems concerning the catalyst such as the decrease in activity due to sintering of iron oxide on account of thermal influences or migration of alkali metal, the increase in pressure drop due to scattering of alkali metal and the like.

SUMMARY OF THE INVENTION

The present inventors have considered the fact that the existing catalysts has a room for improving performances, taken a notice of increasing the activity of the ethylbenzene dehydrogenation catalyst without sacrificing the selectivity, and investigated from various viewpoints mainly for addition of another component to the iron oxide-potassium oxide system catalyst.

Now it has been found out that when a little amount of titanium oxide is added together with other promoter components, the performance remarkably increases, and further its effect not only increases the activity but also fairly increases the selectivity in the same conversion ratio, and its effect does not depend on an adding method of titanium, resulting in completion of the present invention by means of further repeated investigation on the basis of such a knowledge.

PREFERRED EMBODIMENT OF THE INVENTION

Titanium oxide has been found out in the present invention during the investigation with an object of improvement in catalyst performance, and a little amount of addition (0.005 to 0.95 wt. %) provides an unexpected effect of increase in performance, and with respect to a behavior of performance with its addition, the maximum performance is exhibited by a specific adding amount, from which it can be regarded that there is provided a typical promoter effect on the increase in performance, and there is given a particular result which cannot be thought of at all by analogy from Czechoslovakia Patents CS168220 and 174488 in which 1 to 10 wt. % of titanium oxide is added to a catalyst consisting of iron oxide, potassium oxide and vanadium oxide in order to provide the structural stability of the catalyst.

The present inventors have been investigated for catalysts containing Ce, Mo, alkaline earth metal and the like as the promoter components considered to give a high activity and high selectivity in order to further increase the activity, during which it has been found out that when various catalyst raw materials including iron oxide are subjected to wet mixing and kneading followed by extrusion molding to perform drying and calcination thereafter so as to produce a catalyst, the addition and mixing and kneading of titanium oxide can remarkably improve its performance, resulting in achievement of the object.

As the adding method of titanium oxide are available the mixing and kneading method in which titanium oxide itself or a precursor of titanium oxide is added during the wet mixing and kneading step of each of the catalyst materials, or the preceding addition in which titanium oxide is added beforehand in iron oxide by previously adding and dissolving water-soluble titanium salts in an iron salt aqueous solution as a material and then performing necessary following steps to obtain iron oxide in the precipitation method or heat decomposition method which are ordinary industrial iron oxide production methods, however, even existing iron oxide for industry can be used as the iron oxide of the titanium oxide preceding addition provided that titanium oxide of an amount suitable for the object has been already contained.

As the iron salts for producing iron oxide, any salt can be used provided that it is water-soluble such as iron sulfate, iron nitrate, iron halide and the like, however, when iron oxide is produced by the precipitation method, iron sulfate is usually used because of the economic reason, which is produced by a neutralization reaction with a basic substance, wherein in order to make remaining sulfur in iron oxide as less as possible, it is necessary to perform sufficient washing of the precipitate, while when iron oxide is produced by heat decomposition, iron chloride is usually used because of the economic reason and easiness of heat decomposition, however, in order to make remaining chlorine in iron oxide as less as possible, the heat decomposition should be sufficiently carried out to perform production.

The iron raw material to be used for the present catalyst is usually iron oxide, however, iron oxide precursors which can be iron oxide during the calcination of the catalyst, namely iron compounds such as goethite or basic iron carbonate and the like can also be used, or mixtures of these iron compounds and iron oxide can also be used.

The catalyst is finally calcined, so that the components added as the promoter components are not necessarily oxides, for which any compound can be used provided that it can be decomposed into an oxide by heat treatment, however, it is necessary not to contain a component which serves as the catalyst poison, and hence from a viewpoint of availability, economy or the like, it is usually preferable to use hydroxides or carbonates as materials of potassium, cerium and alkali earth metals and to use ammonium paramolybdate or molybdenum oxide for molybdenum.

The content of each of the catalyst components may be one already proposed, which gives, for example, the following range as represented after calculation of all catalyst components into oxides:

| | |
|---|---|
| $Fe_2O_3$ | 40 to 90 wt. % |
| $K_2O$ | 5 to 30 wt. % |
| $Ce_2O_3$ | 2 to 20 wt. % |
| | (including 4.0 to 6.0 wt. %) |
| $MoO_3$ | 1 to 10 wt. % |
| | (including 2.0 to 4.0 wt. %) |
| Alkaline earth metal oxide (e.g. MgO) | 1 to 10 wt. % |
| | (including 1.5 to 4.0 wt. %) | the amount of titanium oxide added as another component is in a range of 0.005 to 0.95 wt. % as represented after calculation of all components into oxides in the same manner irrelevant to the adding method or form of titanium compound to be added.

If the adding amount of titanium oxide is not more than 0.005 wt. %, the increase in performance owing to its addition is not sufficient, while if the adding amount thereof is not less than 0.95 wt. %, the selectivity is greatly improved but the effect of increasing the activity is lowered, and further the long-term stability of performance is lost which is a serious problem from a practical viewpoint, resulting in a catalyst having a disadvantage that the time-dependent decrease in activity is considerable, so that no catalyst can be obtained which can be available for the practical use.

When titanium is added during the mixing and kneading of the catalyst materials, titanium raw materials such as titanium oxide or titanium compounds decomposable to titanium oxide at the final calcination may be used, and further such compounds containing no component which serves as a catalyst poison such as for example titanium nitrate, titanium hydroxide, various titanium alkoxides and the like can be used, while when titanium is subjected to the preceding addition to iron oxide, in the case of iron oxide produced by the precipitation method, the precipitate containing titanium can be subjected to removal of impurities by washing with water, so that any titanium compound can be used provided that it is water-soluble, and for example, titanium compounds such as titanium sulfate, titanium halide, titanium nitrate and the like can be used, and on the other hand, in the case of iron oxide produced by the thermal decomposition method, any titanium compound can be used provided that it is water-soluble, however, it is preferable to use a titanium halide because of its easiness in thermal decomposition.

The catalyst raw materials including iron oxide are subjected to the wet mixing and kneading, wherein it is necessary for the amount of water to be added during mixing and kneading to be an amount of water suitable for the extrusion molding as the following step, the amount of which is different depending on the types of materials to be used, however, addition is usually performed in a range of 10 to 30 wt. %, and a predetermined catalyst can be obtained by performing extrusion molding after sufficient mixing and kneading followed by drying and calcination.

Drying becomes sufficient on condition that free water held by the extrusion molding product can be removed, which is usually performed at a temperature of 80° to 200° C., preferably 100° to 150° C., while calcination is carried out in order that each of the catalyst precursors contained in the dry materials are thermally decomposed and the mechanical strength of the catalyst pellets is improved as well as the performance thereof is increased, which is usually performed in a range of 400° to 1000° C., preferably 500° to 900° C.

The calcination temperature is important for obtaining the catalyst having a good quality, and hence a temperature not more than 400° C. is insufficient for converting each of the catalyst component precursors into oxides, while a temperature not less than 1000° C. promotes the crystal growth of iron oxide resulting in the decrease of activity, which is not preferable.

As a result of measurement of the performance and the performance change with time on stream by conducting the ethylbenzene dehydrogenation reaction using a reaction apparatus of the atmospheric flow system, it has been found out that the effect of addition of a little amount of titanium oxide on the increase in performance is remarkable, there is also provided such an effect that the selectivity in the same conversion ratio is also increased as well as the activity is remarkably increased, and there is provided a performance being stable with time.

As described above, it had been found out that the addition of a little amount of titanium oxide remarkably improves the performance of the catalyst which uses cerium, molybdenum, alkaline earth metal as promoting agents, so that the present inventors further investigated chromium containing catalysts in order to improve performances thereof.

The chromium containing catalyst, which can range between 1.0 and 5.0 wt. % including 2.0 to 4.0 wt. % of the catalyst can be also basically produced by the wet mixing and kneading of each of catalyst component oxides or precursor compounds thereof followed by extrusion molding and then drying and calcination, so that the materials which can be used for the catalyst containing cerium, molybdenum and alkaline earth metal can be used, while as raw materials for chromium are used various chromate salts, especially alkaline salts, ammonium salts and the like of chromate or dichromate, and as other ones can be used oxides of chromium such as chromium oxide, chromic anhydride and the like.

Thus the present inventors prepared a chromium containing catalyst in which titanium oxide is added by means of the same treatment method as that of the catalyst containing cerium, molybdenum and alkaline earth metal.

Using the resultant catalyst, the ethylbenzene dehydrogenation reaction was carried out with a reaction apparatus of the atmospheric flow system and the performance was evaluated, resulting in that the addition of a small amount of titanium oxide remarkably improves the performance of the chromium containing catalyst in the same manner as the case of the catalyst containing cerium, molybdenum and alkaline earth metal, and it has been confirmed that the effect thereof is not only to increase the activity but also to increase the selectivity in the same conversion ratio, and the performance is stable for a long period, resulting in completion of the present invention.

Incidentally, the catalyst according to the present invention is not limited to the utilization as the catalyst for producing styrene by dehydrogenation of ethylbenzene only, which can also be used for the production of various alkenyl aromatic compounds produced by similar dehydrogenation reaction systems, namely divinylbenzene from diethylbenzene, α-methylstyrene from cumene and the like.

According to the present invention, a small amount of titanium oxide is added to the catalyst consisting of iron oxide, potassium oxide and various promoter components, thereby the catalyst activity can be greatly increased, as well as the selectivity in the same conversion ratio can be increased, so that the yield of styrene can be increased thereby without changing operation conditions, and occasionally it becomes possible to operate under more moderate conditions, and hence operational problems such as the decrease in activity due to the crystal growth of iron oxide because of thermal influences, the increase in pressure drop resulting from scattering of potassium and the like can be reduced.

Next, the contents of the present invention will be concretely explained in accordance with Examples, wherein the performance evaluation explained therein was carried out under the following condition:

| Performance evaluation condition | |
|---|---|
| Catalyst volume (cc) | 100 |
| H$_2$O/ethylbenzene (weight ratio) | 2.0 |
| Reaction temperature (°C.) | 570, 600, 620 |
| Reaction time (Hr.) | 100 | the conversion (%) and the selectivity (%) for representing performances are calculated with the following equations, respectively, Conversion (%) = [(A − B)/A] × 100

Selectivity (%) = [C/(A − B)] × 100 the performance change with time on stream was measured at a reaction temperature of 620° C.

Here, A, B and C represent the following substance concentrations, respectively.
- A: ethylbenzene concentration at the catalyst layer inlet (wt. %)
- B: ethylbenzene concentration at the catalyst layer outlet (wt. %)
- C: styrene concentration at the catalyst layer outlet (wt. %)

EXAMPLE 1

500 g of red iron oxide (hematite crystal structure), 252 g of potassium carbonate, 25 g of magnesium carbonate, 55.2 g of cerium hydroxide, 21 g of molybdenum oxide and 0.7 g of titanium oxide were weighed and introduced into a kneader, which were gradually added with pure water with mixing to give a paste state, and then subjected to extrusion molding into a ⅛ inch size, dried in a dryer at 100° to 120° C. overnight, and thereafter transferred to an electric furnace, and calcined at 600° C. for 4 hours.

An obtained catalyst had the following composition:

| Catalyst composition | |
|---|---|
| $Fe_2O_3$ | 67.01 wt. % |
| $K_2O$ | 23.14 |
| $Ce_2O_3$ | 5.36 |
| $MoO_3$ | 2.81 |
| MgO | 1.59 |
| $TiO_2$ | 0.094 | a performance evaluation result of which was as shown in Table 1.

EXAMPLE 2-4

Catalysts of Examples 2, 3 and 4 were prepared by completely the same treating procedure as that of Example 1 except that the using amount of titanium oxide was 0.10 g, 3.0 g or 6.5 g during the wet mixing and kneading of the catalyst materials including iron oxide in Example 1.

Obtained catalysts had the following compositions:

| | Catalyst composition | | |
|---|---|---|---|
| Component (wt. %) | Example 2 | Example 3 | Example 4 |
| $Fe_2O_3$ | 67.17 | 67.47 | 66.82 |
| $K_2O$ | 23.05 | 22.53 | 22.93 |
| $Ce_2O_3$ | 5.37 | 5.28 | 5.18 |
| $MoO_3$ | 2.82 | 2.67 | 2.64 |
| MgO | 1.58 | 1.63 | 1.55 |
| $TiO_2$ | 0.013 | 0.42 | 0.88 | performance evaluation results of which were as shown in Table 1, and a measurement result of the performance change with time on stream for Example 3 was as shown in Table 2.

COMPARATIVE EXAMPLE 1

A catalyst of Comparative example 1 was prepared by completely the same treating procedure as that of Example 1 except that no titanium oxide was added during the wet mixing and kneading of the catalyst materials including iron oxide in Example 1.

An obtained catalyst had the following composition:

| Catalyst composition | |
|---|---|
| $Fe_2O_3$ | 67.43 wt. % |
| $K_2O$ | 22.87 |
| $Ce_2O_3$ | 5.42 |
| $MoO_3$ | 2.58 |
| MgO | 1.70 | a performance evaluation result of which was as shown in Table 1.

COMPARATIVE EXAMPLE 2

A catalyst of Comparative example 2 was prepared by completely the same treating procedure as that of Example 1 except that the adding amount of titanium oxide was 23.0 g during the wet mixing and kneading of the catalyst materials including iron oxide in Example 1.

An obtained catalyst had the following composition:

| Catalyst composition | |
|---|---|
| $Fe_2O_3$ | 65.62 wt. % |
| $K_2O$ | 22.06 |
| $Ce_2O_3$ | 5.09 |
| $MoO_3$ | 2.66 |
| MgO | 1.54 |
| $TiO_2$ | 3.03 | a performance evaluation result of which was as shown in Table 1, and a measurement result of the performance change with time on stream was as shown in Table 2.

EXAMPLE 5

A catalyst of Example 5 was prepared by completely the same treating procedure as that of Example 1 except that 1.57 g of tetrabutoxy titanate [(n-$C_4H_9O)_4Ti$] was used during the wet mixing and kneading of the catalyst materials including iron oxide in Example 1.

An obtained catalyst had the following composition:

| Catalyst composition | |
|---|---|
| $Fe_2O_3$ | 67.57 wt. % |
| $K_2O$ | 23.02 |
| $Ce_2O_3$ | 5.08 |
| $MoO_3$ | 2.57 |
| MgO | 1.71 |
| $TiO_2$ | 0.048 | a performance evaluation result of which was as shown in Table 1.

EXAMPLE 6

500 g of red iron oxide (hematite crystal structure), 84 g of potassium carbonate, 24.0 g of ammonium dichromate and 0.5 g of titanium oxide were weighed and introduced into a kneader, which were gradually added with pure water with mixing to give a paste state, and then subjected to extrusion molding into a ⅛ inch size with an extruder, dried in a dryer at 100° to 120° C. overnight, and thereafter transferred to an electric furnace, and calcined at 600° C. for 4 hours.

An obtained catalyst had the following composition:

| Catalyst composition | |
|---|---|
| $Fe_2O_3$ | 87.46 wt. % |
| $K_2O$ | 10.03 |
| $Cr_2O_3$ | 2.42 |
| $TiO_2$ | 0.087 | the performance evaluation result of which was as shown in Table 1.

EXAMPLES 7-8

Catalysts of Examples 7 and 8 were prepared by completely the same treating procedure as that of Example 6 except that the using amount of titanium oxide was 0.10 g or 2.0 g during the wet mixing and kneading of the catalyst materials including iron oxide in Example 6.

Obtained catalysts had the following compositions:

| | Catalyst composition | |
|---|---|---|
| Component (wt. %) | Example 7 | Example 8 |
| $Fe_2O_3$ | 87.22 | 87.15 |
| $K_2O$ | 10.27 | 10.06 |
| $Cr_2O_3$ | 2.49 | 2.45 |
| $TiO_2$ | 0.018 | 0.34 | performance evaluation results of which were as shown in Table 1, and a measurement result of the performance change with time on stream for Example 8 was as shown in Table 2.

COMPARATIVE EXAMPLE 3

A catalyst of Comparative example 3 was prepared by completely the same treating procedure as that of Example 6 except that no titanium oxide was added during the wet mixing and kneading of the catalyst materials including iron oxide in Example 6.

An obtained catalyst had the following composition:

| Catalyst composition | |
|---|---|
| $Fe_2O_3$ | 87.53 wt. % |
| $K_2O$ | 9.98 |
| $Cr_2O_3$ | 2.49 | a performance evaluation result of which was as shown in Table 1.

COMPARATIVE EXAMPLE 4

A catalyst of Comparative example 4 was prepared by completely the same treating procedure as that of Example 6 except that the adding amount of titanium oxide was 13.0 g during the wet mixing and kneading of the catalyst materials including iron oxide in Example 6.

An obtained catalyst had the following composition:

| Catalyst composition | |
|---|---|
| $Fe_2O_3$ | 85.58 wt. % |

*-continued*

| Catalyst composition | |
|---|---|
| $K_2O$ | 9.74 |
| $Cr_2O_3$ | 2.43 |
| $TiO_2$ | 2.25 | a performance evaluation result of which was as shown in Table 1, and a measurement result of the performance change with time on stream was as shown in Table 2.

EXAMPLE 9

1741 g of ferrous sulfate and 0.75 g of titanium sulfate were weighed and introduced into a 10 l beaker, and then 6 l of pure water was added with agitation to be dissolved (to give a solution A), separately from which 4 l of pure water was added beforehand in a 5 l beaker, and 796.5 g of sodium carbonate having been weighed was gradually added with agitation to be dissolved (to give a solution B).

Next, the solution A is gradually added to the solution B with agitation at an ordinary temperature to obtain a precipitate of basic iron carbonate (a dropping period of the solution A was 60 minutes), which was left for 1-2 hours, and washing with water and filtration were repeated, thereby impurities were sufficiently removed followed by transfer to a porcelain plate so as to dry in a dryer at 100° to 120° C. overnight, and further the dried material was introduced into an electric furnace to calcine at 400° C. for 4 hours, thereby iron oxide containing titanium oxide was obtained.

The whole amount of the iron oxide was transferred to a kneader, and as other catalyst materials were weighed 252 g of potassium carbonate, 25 g of magnesium carbonate, 134.3 g of cerium carbonate and 21 g of molybdenum oxide which were introduced into the kneader, and pure water was gradually added with agitation to give a paste state, and then the mixed and kneaded material was subjected to extrusion molding into a ⅛ inch size with an extruder, which was dried in a dryer at 100° to 120° C. overnight, and calcined in an electric furnace at 600° C. for 4 hours.

An obtained catalyst had the following composition:

| Catalyst composition | |
|---|---|
| $Fe_2O_3$ | 67.11 wt. % |
| $K_2O$ | 23.05 |
| $Ce_2O_3$ | 5.36 |
| $MoO_3$ | 2.80 |
| $MgO$ | 1.64 |
| $TiO_2$ | 0.034 | a performance evaluation result of which was as shown in Table 1.

EXAMPLE 10-12

Catalysts of Examples 10, 11 and 12 were prepared by completely the same treating procedure as that of Example 9 except that the using amount of titanium sulfate was 0.15 g, 3.4 g or 18.5 g during the preparation of iron oxide containing titanium oxide in Example 9.

Obtained catalysts had the following compositions:

| | Catalyst composition | | |
|---|---|---|---|
| Component (wt. %) | Example 10 | Example 11 | Example 12 |
| $Fe_2O_3$ | 67.05 | 67.09 | 66.57 |

-continued

| Component (wt. %) | Catalyst composition | | |
|---|---|---|---|
| | Example 10 | Example 11 | Example 12 |
| K₂O | 23.20 | 23.03 | 22.91 |
| Ce₂O₃ | 5.28 | 5.29 | 5.32 |
| MoO₃ | 2.81 | 2.83 | 2.79 |
| MgO | 1.65 | 1.61 | 1.58 |
| TiO₂ | 0.007 | 0.15 | 0.82 | performance evaluation results of which were as shown in Table 1, and a measurement result of the performance change with time on stream for Example 12 was as shown in Table 2.

COMPARATIVE EXAMPLE 5

A catalyst of Comparative example 5 was prepared by completely the same treating procedure as that of Example 9 except that no titanium sulfate was added during the preparation of iron oxide containing titanium oxide in Example 9.

An obtained catalyst had the following composition:

| Catalyst composition | |
|---|---|
| Fe₂O₃ | 67.09 wt. % |
| K₂O | 23.03 |
| Ce₂O | 5.41 |
| MoO₃ | 2.85 |
| MgO | 1.61 | a performance evaluation result of which was as shown in Table 1.

COMPARATIVE EXAMPLE 6

A catalyst of Comparative example 6 was prepared by completely the same treating procedure as that of Example 9 except that the using amount of titanium sulfate was 37.5 g during the preparation of iron oxide containing titanium oxide in Example 9.

An obtained catalyst had the following composition:

| Catalyst composition | |
|---|---|
| Fe₂O₃ | 66.02 wt. % |
| K₂O | 22.74 |
| Ce₂O₃ | 5.29 |
| MoO₃ | 2.75 |
| MgO | 1.57 |
| TiO₂ | 1.63 | a performance evaluation result of which was as shown in Table 1, and a measurement result of the performance change with time on stream was as shown in Table 2.

TABLE 1

| | Performance evaluation results of catalysts | | | | | |
|---|---|---|---|---|---|---|
| | 570° C. | | 600° C. | | 620° C. | |
| Catalyst | Conversion % | Selectivity % | Conversion % | Selectivity % | Conversion % | Selectivity % |
| Example | | | | | | |
| 1 | 49.5 | 97.0 | 68.6 | 95.4 | 76.3 | 93.5 |
| 2 | 42.6 | 96.9 | 62.4 | 95.5 | 73.5 | 93.4 |
| 3 | 48.3 | 97.1 | 68.7 | 95.3 | 75.0 | 93.7 |
| 4 | 46.2 | 97.5 | 66.4 | 96.2 | 76.8 | 94.0 |
| 5 | 44.0 | 97.8 | 64.5 | 96.5 | 74.8 | 94.3 |
| 6 | 47.7 | 95.0 | 64.4 | 93.3 | 74.3 | 91.0 |
| 7 | 42.6 | 95.1 | 61.7 | 93.2 | 71.8 | 91.6 |
| 8 | 49.3 | 95.1 | 66.2 | 93.3 | 75.4 | 91.2 |
| 9 | 49.6 | 96.8 | 67.8 | 95.3 | 76.5 | 93.5 |
| 10 | 43.2 | 96.6 | 60.8 | 95.5 | 73.0 | 93.4 |
| 11 | 47.3 | 96.8 | 67.5 | 95.2 | 75.8 | 93.7 |
| 12 | 44.0 | 97.2 | 64.6 | 95.7 | 75.9 | 94.0 |
| Com. ex. | | | | | | |
| 1 | 38.8 | 96.9 | 60.5 | 95.6 | 71.7 | 93.8 |
| 2 | 40.1 | 97.7 | 61.5 | 96.2 | 71.3 | 94.6 |
| 3 | 41.1 | 95.0 | 60.5 | 93.4 | 71.2 | 91.3 |
| 4 | 44.2 | 95.7 | 64.1 | 93.7 | 73.0 | 91.7 |
| 5 | 39.2 | 96.5 | 60.1 | 95.2 | 70.9 | 93.3 |
| 6 | 42.2 | 97.4 | 63.0 | 95.8 | 73.0 | 94.1 |

TABLE 2

| | Measurement results of the performance change with time on stream (conversion, %) | | | | | |
|---|---|---|---|---|---|---|
| | Time on stream (Hr.) | | | | | |
| Catalyst | 100 | 150 | 200 | 300 | 400 | 500 |
| Example | | | | | | |
| 3 | 75.0 | 74.5 | 74.1 | 73.7 | 73.4 | 72.9 |
| 8 | 75.4 | 75.1 | 74.8 | 74.6 | 74.3 | 74.0 |
| 12 | 75.9 | 75.8 | 75.5 | 74.7 | 74.0 | 73.1 |
| Com. ex. | | | | | | |
| 2 | 71.3 | 70.7 | 68.9 | 67.8 | 66.5 | 65.6 |
| 4 | 73.0 | 71.7 | 71.2 | 69.9 | 68.7 | 68.0 |
| 6 | 73.0 | 71.1 | 70.3 | 69.1 | 68.0 | 67.9 |

What is claimed is:

1. An alkyl aromatic hydrocarbon dehydrogenation catalyst containing iron oxide, potassium oxide and titanium oxide as essential components wherein an iron oxide content is 40.0 to 90.0 wt. %, a potassium oxide content is 5.0 to 30.0 wt. % and a titanium oxide content is 0.005 to 0.95 wt. % provided that all catalyst components are calculated as oxides.

2. The catalyst according to claim 1 wherein cerium oxide, molybdenum oxide and magnesium oxide are contained as promoter components, and a cerium oxide content is 2.0 to 20.0 wt. %, a molybdenum oxide content is 1.0 to 10.0 wt. % and a magnesium oxide content is 1.0 to 10.0 wt. % provided that all catalyst components are calculated as oxides.

3. The catalyst according to claim 1 wherein cerium oxide, molybdenum oxide and magnesium oxide are contained as promoter components, and a cerium oxide content is 4.0 to 6.0 wt. %, a molybdenum oxide content is 2.0 to 4.0 wt. % and a magnesium oxide content is 1.5 to 4.0 wt. % provided that all catalyst components are calculated as oxides.

4. The catalyst according to claim 1 wherein chromium oxide is contained as a promoter component, and a chromium oxide content is 1.0 to 5.0 wt. % provided that all catalyst components are calculated as oxides.

5. The catalyst according to claim 1 wherein chromium oxide is contained as a promoter component, and a chromium oxide content is 2.0 to 4.0 wt. % provided that all catalyst components are calculated as oxides.

6. The catalyst according to claim 1 wherein the alkyl aromatic hydrocarbon is selected from ethylbenzene, diethylbenzene and cumene.

7. A method for producing the catalyst according to claim 1 wherein catalyst component oxides and/or catalyst component oxide precursor compounds are subjected to wet mixing and kneading followed by extrusion molding, which are subsequently dried and calcined.

* * * * *